United States Patent
Swenson (10) Patent No.: US 7,803,549 B2
(45) Date of Patent: Sep. 28, 2010

(54) CONTROLS FOR PRIMERS IN MULTIPLEX AMPLIFICATION REACTIONS

(75) Inventor: David Swenson, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 12/169,463

(22) Filed: Jul. 8, 2008

(65) Prior Publication Data

US 2008/0286798 A1    Nov. 20, 2008

Related U.S. Application Data

(62) Division of application No. 10/721,579, filed on Nov. 24, 2003, now Pat. No. 7,410,760.

(60) Provisional application No. 60/429,834, filed on Nov. 27, 2002.

(51) Int. Cl.
*C12Q 1/68* (2006.01)

(52) U.S. Cl. .................. 435/6; 435/91.1; 435/91.2; 536/23.1; 536/24.33

(58) Field of Classification Search .................. None
See application file for complete search history.

(56) References Cited

OTHER PUBLICATIONS

The Stratagene Catalog p. 39. 1988.*
Mutasa et al., Single-Tube, Nested PCR for the Diagnosis of *Polymyxa betae* Infection in Sugar Beet Roots and Colorimetric Analysis of Amplified Products, 1996, Phytopathology, vol. 86, No. 5, pp. 493-497.
Kong et al., "Identification of Oligonucleotide Primers Targeted at the 16S-23S rDNA Intergenic Spacers for Genus- and Species-specific Detection of Aeromonads," 1999, vol. 38, No. 9, pp. 802-808.

* cited by examiner

*Primary Examiner*—Heather G Calamita
(74) *Attorney, Agent, or Firm*—Townsend and Townsend and Crew LLP (57) ABSTRACT

The present invention provides methods and compositions for confirming the integrity of primers and other components of amplification reactions, including multiplex amplification reactions.

14 Claims, 5 Drawing Sheets

SEQUENCE LISTING

<160> NUMBER OF SEQ ID NOS: 15

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence:Bacteria A
      specific PCR target sequence

<400> SEQUENCE: 1
ggtgcggaag tgtaacgagg tggaaagcgc accatcgttt ctattacaag tcccttgatg      60
gaagattatg tcgaccactt t      81

<210> SEQ ID NO 2
<211> LENGTH: 81
<212> TYPE: DNA
<213> ORGANISM: Artificial Sequence
<220> FEATURE:

-continued

<223> OTHER INFORMATION: Description of Artificial Sequence:
      complementary sequence to the target sequence for Bacteria A

<400> SEQUENCE: 2
aaagtggtcg acataatctt ccatcaaggg actagtaata gaaacgatgg tgcgctttcc    60
acctcgttac acttccgcac c                                              81

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:Bacteria A
      forward primer

<400> SEQUENCE: 3
ttacacttcc gcacc                                                     15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:Bacteria A
      reverse primer

<400> SEQUENCE: 4
tatgtcgacc acttt                                                     15

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:Beacons
      probe for Bacteria A
<220> FEATURE:
<221> NAME/KEY: modified_base
<222> LOCATION: (1)
<223> OTHER INFORMATION: n = c modified by FAM
<220> FEATURE:
<221> NAME/KEY: modified_base
<222> LOCATION: (27)
<223> OTHER INFORMATION: n = g modified by Dabcyl

<400> SEQUENCE: 5
ncacgcacta gtaatagaaa cgcgtgn                                        27

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence:Bacteria B
      specific PCR target sequence

<400> SEQUENCE: 6
gcacgcgtat gcagcgacga tgcagcgacg agtcgaggct aggcgagcag ctttatctat    60
catcgtgatc gtgtacgtag ctagcatctg                                     90

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence:
      complementary sequence to the target sequence for Bacteria B

```
<400> SEQUENCE: 7
cagatgctag ctacgtacac gatcacgatg atagataaag ctgctcgcct agcctcgact    60
cgtcgctgca tcgtcgctgc atacgcgtgc                                    90

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:Bacteria B
      forward primer

<400> SEQUENCE: 8
gctgcatacg cgtgc                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:Bacteria B
      reverse primer, Target 2 reverse primer sequence

<400> SEQUENCE: 9
cgtagctagc atctg                                                    15

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Beacons
      probe for Bacteria B
<220> FEATURE:
<221> NAME/KEY: modified_base
<222> LOCATION: (1)
<223> OTHER INFORMATION: n = c modified by Texas Red
<220> FEATURE:
<221> NAME/KEY: modified_base
<222> LOCATION: (30)
<223> OTHER INFORMATION: n = g modified by Dabcyl

<400> SEQUENCE: 10
ncacgcgctg ctcgcctagc ctcggcgtgn                                    30

<210> SEQ ID NO 11
<211> LENGTH: 111
<212> TYPE: DNA
<213> ORGANISM: Artificial Sequence
<220> FEATURE:
<223> OTHER INFORMATION: Description of Artificial Sequence:Internal
      Control Oligo

<400> SEQUENCE: 11
ggtgcggaag tgtaaaaacg tagctagcat aaaagctagc atctgaaatc gagctgatgc    60
tgcaaagctg catacgcgaa agcatacgcg tgcaaatatg tcgaccactt t           111

<210> SEQ ID NO 12
<211> LENGTH: 111
<212> TYPE: DNA
<213> ORGANISM: Artificial Sequence
<220> FEATURE:
<223> OTHER INFORMATION: Description of Artificial Sequence:
      complementary sequence to the target sequence for Internal
      Control Oligo
```

```
<400> SEQUENCE: 12
aaagtggtcg acatatttgc acgcgtatgc tttcgcgtaa gcagctttgc agcatcagct        60
cgatttcaga tgctagcttt tatgctagct acgtttttac acttccgcac c                111

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:Beacons
      probe for the Internal Control
<220> FEATURE:
<221> NAME/KEY: modified_base
<222> LOCATION: (1)
<223> OTHER INFORMATION: n = c modified by TET
<220> FEATURE:
<221> NAME/KEY: modified_base
<222> LOCATION: (27)
<223> OTHER INFORMATION: n = g modified by Dabcyl

<400> SEQUENCE: 13
ncacgcgcag catcagctcg agcgtgn                                            27

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Target 2
      reverse primer subsequences

<400> SEQUENCE: 14
cgtagctagc atctgaaaag ctagcatctg                                         30

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:Target 2
      reverse primer subsequences
<220> FEATURE:
<221> NAME/KEY: modified_base
<222> LOCATION: (10)..(21)
<223> OTHER INFORMATION: n = g, a, c or t; unrelated nucleotides
      separating Target 2 reverse primer subsequences

<400> SEQUENCE: 15
cgtagctagn nnnnnnnnnn ncatctg                                            27
```

CONTROLS FOR PRIMERS IN MULTIPLEX AMPLIFICATION REACTIONS

CROSS-REFERENCE TO RELATED APPLICATION

The present application is a divisional application of U.S. patent application Ser. No. 10/721,579, filed on Nov. 24, 2003, which claims the benefit of priority to U.S. Provisional Patent Application No. 60/429,834, filed Nov. 27, 2002, each of which is incorporated by reference in its entirety for all purposes.

FIELD OF THE INVENTION

This invention relates to controls used to confirm primer integrity in an amplification reaction.

BACKGROUND OF THE INVENTION

Methods for amplifying nucleic acids provide useful tools for the detection of human pathogens, detection of human genetic polymorphisms, detection of RNA and DNA sequences, for molecular cloning, sequencing of nucleic acids, and the like. In particular, the polymerase chain reaction (PCR) has become an important tool in the cloning of DNA sequences, forensics, paternity testing, pathogen identification, disease diagnosis, and other useful methods where the amplification of a nucleic acid sequence is desired. See e.g., PCR Technology: Principles and Applications for DNA Amplification (Erlich, ed., 1992); PCR Protocols: A Guide to Methods and Applications (Innis et al., eds, 1990).

PCR permits the copying, and resultant amplification, of a target nucleic acid. Briefly, a target nucleic acid, e.g. DNA, is combined with a sense and antisense primers, dNTPs, DNA polymerase and other reaction components. See Innis et al. The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

A variety of factors can lead to non-functional PCR or other amplification reactions. For example, endonucleases may cleave the primers used to amplify a polynucleotide. In such an event, the user is unable to distinguish between the lack of an amplification product resulting from the absence of the appropriate template or a false negative result caused by primer cleavage. The present invention addresses this and other problems.

BRIEF SUMMARY OF THE INVENTION

This invention provides methods of testing the integrity of primers in a multiplex amplification reaction, wherein the amplification reaction comprises primers sufficient to amplify at least two different target sequences. In some embodiments, the method comprises, providing in a mixture the primers and a single-stranded polynucleotide sequence comprising the sequences of the primers, subsequences of the primers at least five nucleotides long, or complements of the sequences of the primers; amplifying the polynucleotide sequence; and detecting the presence or absence of the amplified polynucleotide, thereby testing the integrity of the primers in the amplification reaction.

In some embodiments, the target sequences are less than 50% identical to each other. In some embodiments, the single-stranded polynucleotide sequence is provided by denaturing a double-stranded polynucleotide.

In some embodiments, the single-stranded polynucleotide sequence is a synthetic single-stranded polynucleotide. In some embodiments, the single-stranded polynucleotide sequence comprises the primer sequences. In some embodiments, the single-stranded polynucleotide sequence comprises subsequences of the primers at least five nucleotides long. In some embodiments, the single-stranded polynucleotide sequence comprises all subsequences of the primers that are nine nucleotides long. In some embodiments, the single-stranded polynucleotide comprises at least two subsequences of each primer, wherein the combination of the at least two subsequences contain every nucleotide of the primer sequence.

In some embodiments, the single-stranded polynucleotide sequence comprises two subsequences of a primer sequence and at least the last two nucleotides of a first subsequence are identical to the first at least two nucleotides of a second subsequence. In some embodiments, at least the last five nucleotides of the first subsequence are identical to at least the first five nucleotides of the second subsequence.

In some embodiments, the mixture comprises at least a first, second, and third primer and the single-stranded polynucleotide sequence comprises the sequences of the at least first, second and third primer or subsequences at least five nucleotides long of the at least first, second and third primers.

In some embodiments, the mixture comprises primers sufficient to amplify at least three target sequences. In some embodiments, the amplification of the target sequences is performed in the same reaction as the amplification of the single-stranded polynucleotide sequence.

In some embodiments, the mixture comprises a first primer pair and the single-stranded polynucleotide sequence comprises sequences, or complement thereof, of primers of the first primer pair oriented such that the first primer pair is capable of amplifying the remaining primer sequences, or subsequences thereof, in the single-stranded polynucleotide. In some embodiments, the mixture comprises at least a second primer pair comprising a forward and a reverse primer, wherein the single-stranded polynucleotide sequence comprises sequences or subsequences of the at least second primer pair oriented such that the reverse primer sequence or subsequence is closer to the 5' end of the polynucleotide sequence than the forward primer sequence or subsequence.

In some embodiments, the single-stranded polynucleotide sequence comprises subsequences of the primers at least five nucleotides long. In some embodiments, the single-stranded polynucleotide sequence comprises all subsequences of the primers that are nine nucleotides long.

The present invention also provides reagent kits comprising: (i.) amplification reagents comprising primers sufficient to amplify at least two different target sequences; (ii.) a polynucleotide sequence comprising the sequences of the primers or subsequences of the primers at least five nucleotides long; and (iii.) at least one probe for detecting the polynucleotide sequence.

In some embodiments, the polynucleotide sequence is single-stranded. In some embodiments, the polynucleotide sequence comprises the primer sequences. In some embodiments, the polynucleotide sequence comprises subsequences of the primers at least five nucleotides long. In some embodiments, the amplification reagents comprise a first primer pair and the single-stranded polynucleotide sequence comprises sequences, or complement thereof, of primers of the first primer pair oriented such that primer pair is capable of amplifying the remaining primer sequences, or subsequences thereof, in the single-stranded polynucleotide.

In some embodiments, the amplification reagents comprise at least a second primer pair comprising a forward and a reverse primer, wherein the single-stranded polynucleotide sequence comprises sequences or subsequences of the at least second primer pair oriented such that the reverse primer sequence or subsequence is closer to the 5' end of the polynucleotide sequence than the forward primer sequence or subsequence. In some embodiments, the single-stranded polynucleotide sequence comprises subsequences of the primers at least five nucleotides long.

In some embodiments, the polynucleotide sequence comprises all subsequences of the primers that are nine nucleotides long. In some embodiments, the polynucleotide sequence comprises two subsequences of a primer sequence and at least the last two nucleotides of a first subsequence are identical to the first at least two nucleotides of a second subsequence.

In some embodiments, at least the last five nucleotides of the first subsequence are identical to at least the first five nucleotides of the second subsequence.

In some embodiments, the kit comprises at least a first, second, and third primer and the single-stranded polynucleotide sequence comprises the sequences of the at least first, second and third primer or subsequences at least five nucleotides long of the at least first, second and third primers. In some embodiments, the reagent kit comprises a first primer pair and the polynucleotide sequence comprises sequences of primers of the first primer pair oriented such that the first primer pair is capable of amplifying the remaining primer sequences, or subsequences thereof, in the single-stranded polynucleotide.

In some embodiments, the kit comprises at least a second primer pair comprising a forward and a reverse primer, and the single-stranded polynucleotide sequence comprises sequences or subsequences of the at least second primer pair oriented such that the reverse primer sequence or subsequence is closer to the 5' end of the polynucleotide sequence than the forward primer sequence or subsequence.

In some embodiments, the single-stranded polynucleotide sequence comprises subsequences of the primers at least five nucleotides long. In some embodiments, the single-stranded polynucleotide sequence comprises all subsequences of the primers that are nine nucleotides long.

DEFINITIONS

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683,195 and 4,683,202; PCR Protocols: A Guide to Methods and Applications (Innis et al., eds, 1990)), strand displacement amplification (SDA) (Walker, et al. Nucleic Acids Res. 20(7): 1691-6 (1992); Walker PCR Methods Appl 3(1):1-6 (1993)), transcription-mediated amplification (Phyffer, et al., J. Clin. Microbiol. 34:834-841 (1996); Vuorinen, et al., J. Clin. Microbiol. 33:1856-1859 (1995)), nucleic acid sequence-based amplification (NASBA) (Compton, Nature 350(6313): 91-2 (1991), rolling circle amplification (RCA) (Lisby, Mol. Biotechnol. 12(1):75-99 (1999)); Hatch et al., Genet. Anal. 15(2):35-40 (1999)) and branched DNA signal amplification (bDNA) (see, e.g., Iqbal et al., Mol. Cell Probes 13(4):315-320 (1999)).

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification reaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

"Multiplex amplification" refers to amplification of multiple polynucleotide fragments in the same reaction.

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 25 nucleotides. The "integrity" of a primer refers to the ability of the primer to primer an amplification reaction. For example, the integrity of a primer is typically no longer intact after degradation of the primer sequences such as by endonuclease cleavage.

A "probe" refers to a polynucleotide sequence capable of hybridization to a polynucleotide sequence of interest and allows for the detecting of the polynucleotide sequence of choice. For example, "probes" can comprise polynucleotides linked to fluorescent or radioactive reagents, thereby allowing for the detection of these reagents.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

The phrase "nucleic acid" or "polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Two nucleic acid sequences or polypeptides are said to be "identical" if the sequence of nucleotides or amino acid residues, respectively, in the two sequences is the same when aligned for maximum correspondence as described below. The term "complementary to" is used herein to mean all of a first sequence is complementary to at least a portion of a reference polynucleotide sequence.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. The percent identity between two sequences can be represented by any integer from 25% to 100%. More preferred embodiments include at least: 25%, 30%, 35%, 40%, 45%, 50%, 55%, 60%, 65%, 70%, 75%, 80%, 85%, 90%, 95%, or 99%.

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

DETAILED DESCRIPTION

I. Introduction

This invention provides methods and kits to control for the integrity of components of an amplification reaction. The invention provides a control polynucleotide that contains sequences or subsequences of primers used in an amplification reaction. By confirming the integrity of the control polynucleotide, the integrity of primers in an amplification is also determined. The integrity of the control polynucleotide is confirmed by detecting the amplification of the control polynucleotide in the amplification reaction.

II. Control Polynucleotides of the Invention

The control polynucleotides of the invention are used to monitor for the presence of factors that degrade primers. For example, in some cases, sequence-specific endonucleases will specifically degrade a primer, thereby preventing amplification of the corresponding target polynucleotide. The presence or absence of the control polynucleotide allows for a determination of whether the lack of accumulation of a target polynucleotide is due to lack of a target template or due to defects in the amplification reagents, including degradation of primers. Thus, if no target is amplified, accumulation of the control polynucleotide amplification product indicates that the primer sequences have not been degraded. Alternatively, if the control polynucleotide is not amplified, then there is reason to believe that the amplification reagents such as the primers were defective and that the reaction needs to be repeated.

The control polynucleotide is typically single-stranded during or before at least part of the amplification reaction so as to control for endonucleases that cleave single-stranded, but not double-stranded, nucleic acids. Thus, single-stranded control polynucleotides can be provided in the reaction mixture. Alternatively, the polynucleotide can be provided first in double-stranded form and then denatured (for instance, with heat) prior to the amplification reaction, thereby providing the control polynucleotide in single-stranded form.

The control polynucleotide typically comprises at least three different components. First, the control polynucleotide contains a probe binding site. This site is typically recognized by a probe that does not hybridize to any other sequence in the amplification reaction. The presence of the probe binding site allows for detection of the amplified control polynucleotide. As discussed below, the probe can be any chemical reagent that allows for the detection of the accumulation of an amplification product. Exemplary probes, include, e.g., fluorescence-based probes such as Taqman®-based probes or molecular beacons.

In addition, the control polynucleotide will include at least one set of primer binding sequences that can be used to amplify the control polynucleotide. Thus, the control polynucleotide will contain a first sequence that is at least homologous to or complementary to a forward primer sequence and a second sequence that is closer to the 3' end of the control polynucleotide that is at least homologous to or complementary to a reverse primer sequence such that the forward primer and the reverse primer will allow for amplification of the control polynucleotide. While not required for the function of the invention, the forward and reverse primers will typically be the same primers that are used to amplify one target polynucleotide in the amplification reaction.

In cases where multiplex amplification reactions are performed, the control polynucleotide also comprises nucleotide sequences corresponding to at least a subsequence of the remaining primer sequences in the multiplex amplification reaction. Each of these sequences are found between the primers used to amplify the control polynucleotide and therefore are referred to herein as "internal" primer sequences or subsequences. Typically, the control polynucleotide comprises the sequence or at least a subsequence of each primer used in the multiplex amplification reaction.

While the primer sequences used to amplify the control polynucleotide are intact and oriented so as to amplify the control polynucleotide, the remaining primer sequences are typically oriented and constructed such that no amplification products are produced from hybridization of primers onto the sequences. For example, the sequences or subsequences of a internal reverse primer can be closer to the 3' or 5' end of the control polynucleotide compared to the sequences or subsequences of a forward internal primer. The probe binding site can separate different internal primer sequences or subsequences or all of the sequences or subsequences can be 5' or 3' of the probe binding site.

Figure 1:
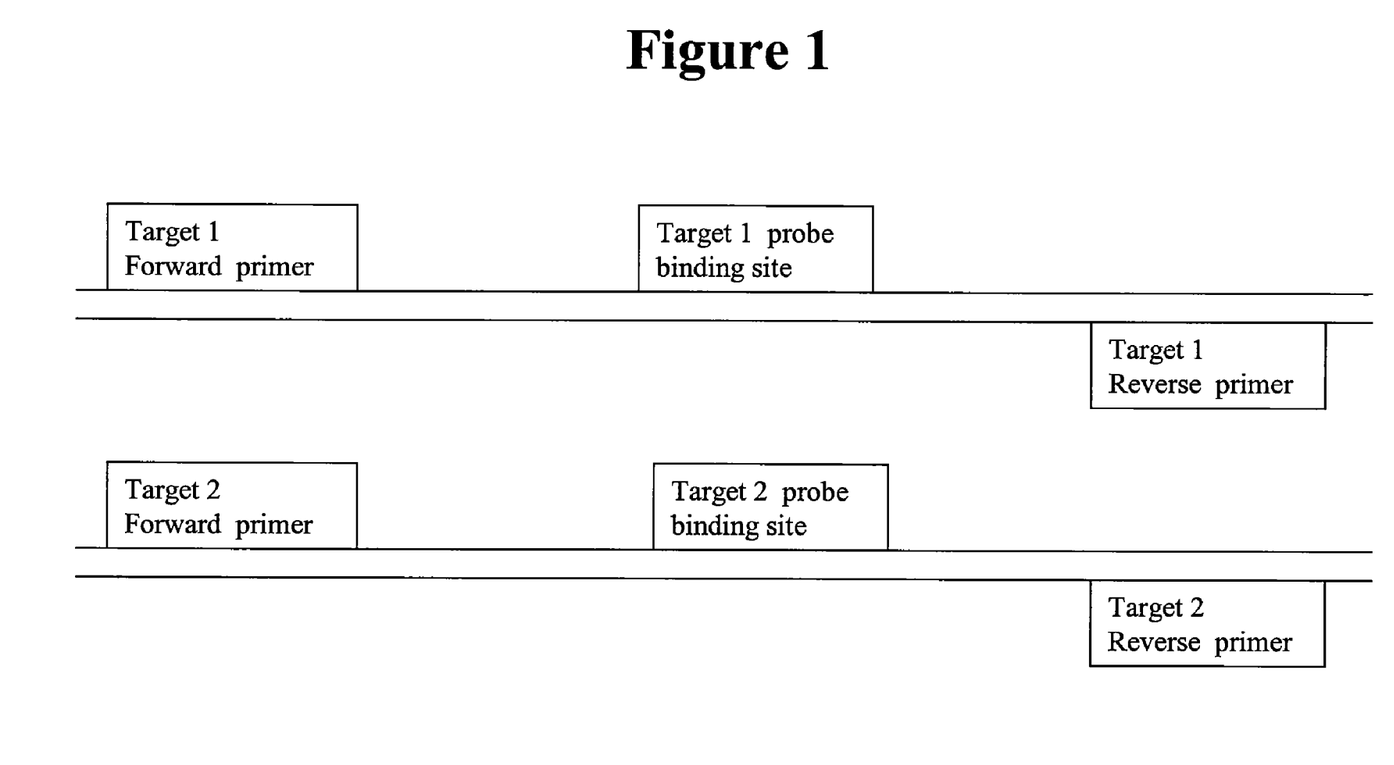
FIG. 1 illustrates a design for a multiplex amplification reaction comprising three double-stranded target sequences, each containing a probe binding site and a binding site for a forward and reverse primer.
Figure 2:
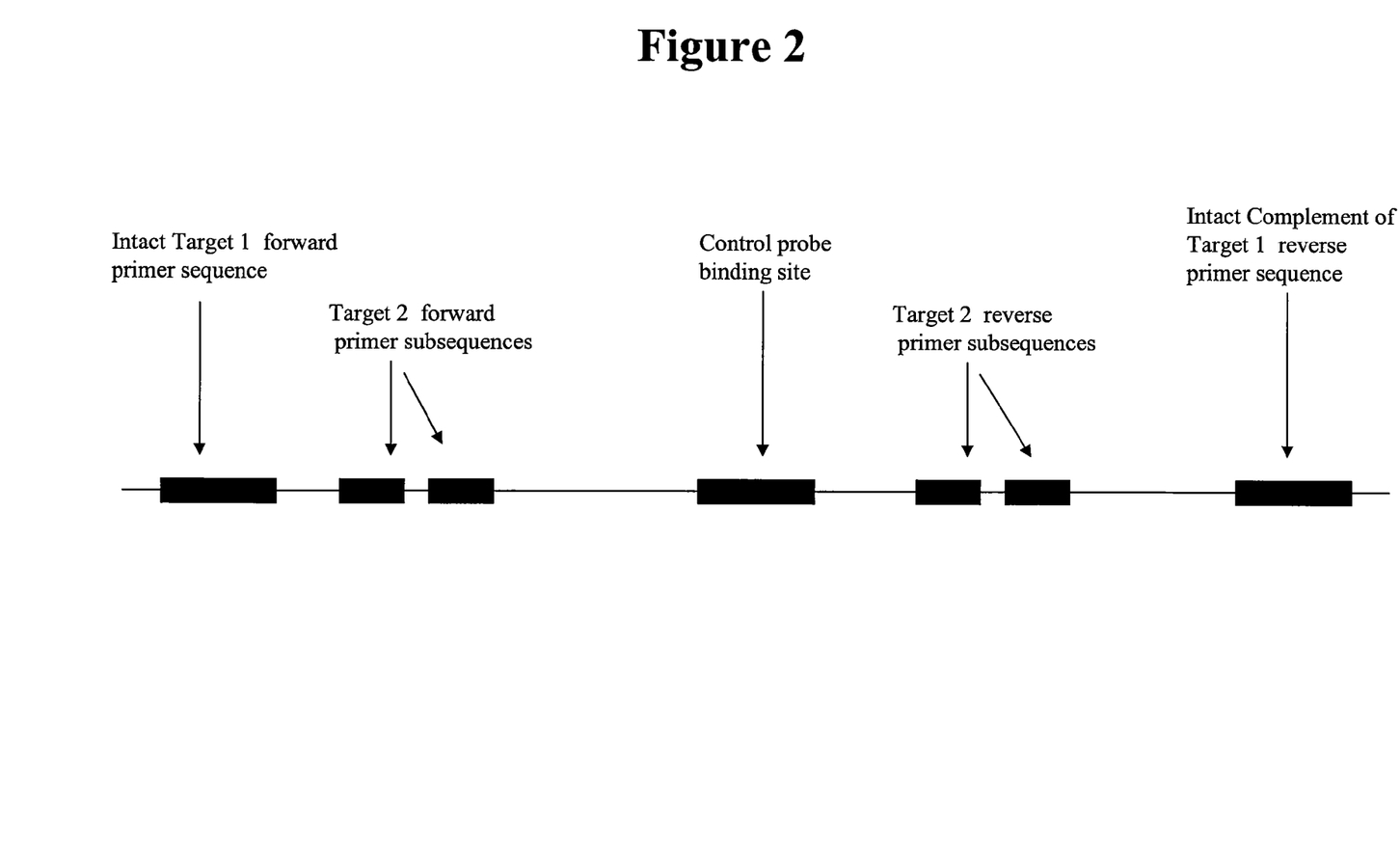
FIG. 2 illustrates one possible design of a single-stranded control polynucleotide. The polynucleotide is designed such that primers for amplification of a first target ("Target 1") also amplifies the single-stranded polynucleotide. Primer sequences for amplifying a second target ("Target 2") are divided into subsequences that are present in the single-stranded polynucleotide. In this FIG. 2, the Target 2 forward primer subsequences are present 5' of the Target 2 reverse primer subsequences on the single-stranded polynucleotide.
Figure 3:
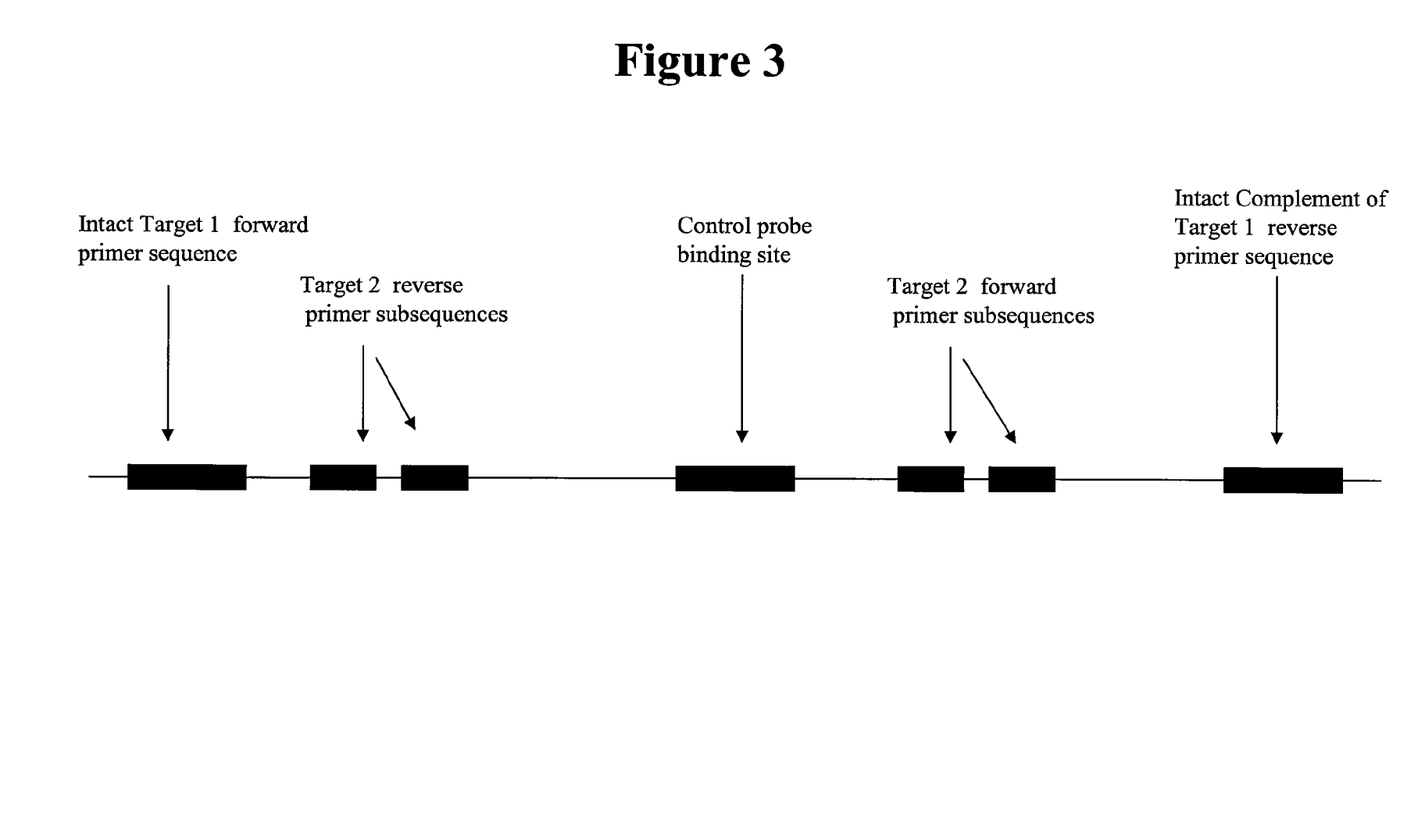
FIG. 3 illustrates one possible design of a single-stranded control polynucleotide. The polynucleotide is designed such that primers for amplification of a first target ("Target 1") also amplifies the single-stranded polynucleotide. Primer sequences for amplifying a second target ("Target 2") are divided into subsequences that are present in the single-stranded polynucleotide. In this FIG. 3, the Target 2 reverse primer subsequences are present 5' of the Target 2 forward primer subsequences on the single-stranded polynucleotide.

FIGS. 1-3 illustrate various designs for control polypeptides used to control for primer degradation in a multiplex amplification reaction comprising the two target polynucleotides in FIG. 1. FIG. 1 illustrates two targets in a multiplex amplification reaction as well as probes that specifically bind and detect each target amplification product and the forward and reverse primers used to amplify each target. FIGS. 2 and 3 illustrate alternative possible orientations for internal primer sequences. In FIG. 2, the forward and reverse primers for Target 1 are used to amplify the control polynucleotide. In addition, the control polynucleotide contains sequences of the forward and reverse primers that are used to amplify Target 2. In FIG. 2, the Target 2 primer sequences are divided up into subsequences (as discussed more fully below) and are oriented such that the forward sequences are closer to the 5' end of the control polynucleotide than the reverse sequences. FIG. 3 illustrates alternate embodiments, where the reverse primer sequences for the internal primer are closer to the 5' end of the control polynucleotide than the forward primer sequence of the internal primer.

In some aspects, some or all of the internal primer sequences are contained in the control polynucleotide as subsequences of the primer sequences. In these embodiments, the subsequences of an internal primer sequences can represent some or all of the internal primer sequences. For example, a particular internal primer sequence can be represented by a single subsequence that contains some but not all of the primer sequence. More typically, an internal primer sequence will be represented by two or more subsequences, which when combined, include the entire internal primer sequence.

Figure 4:
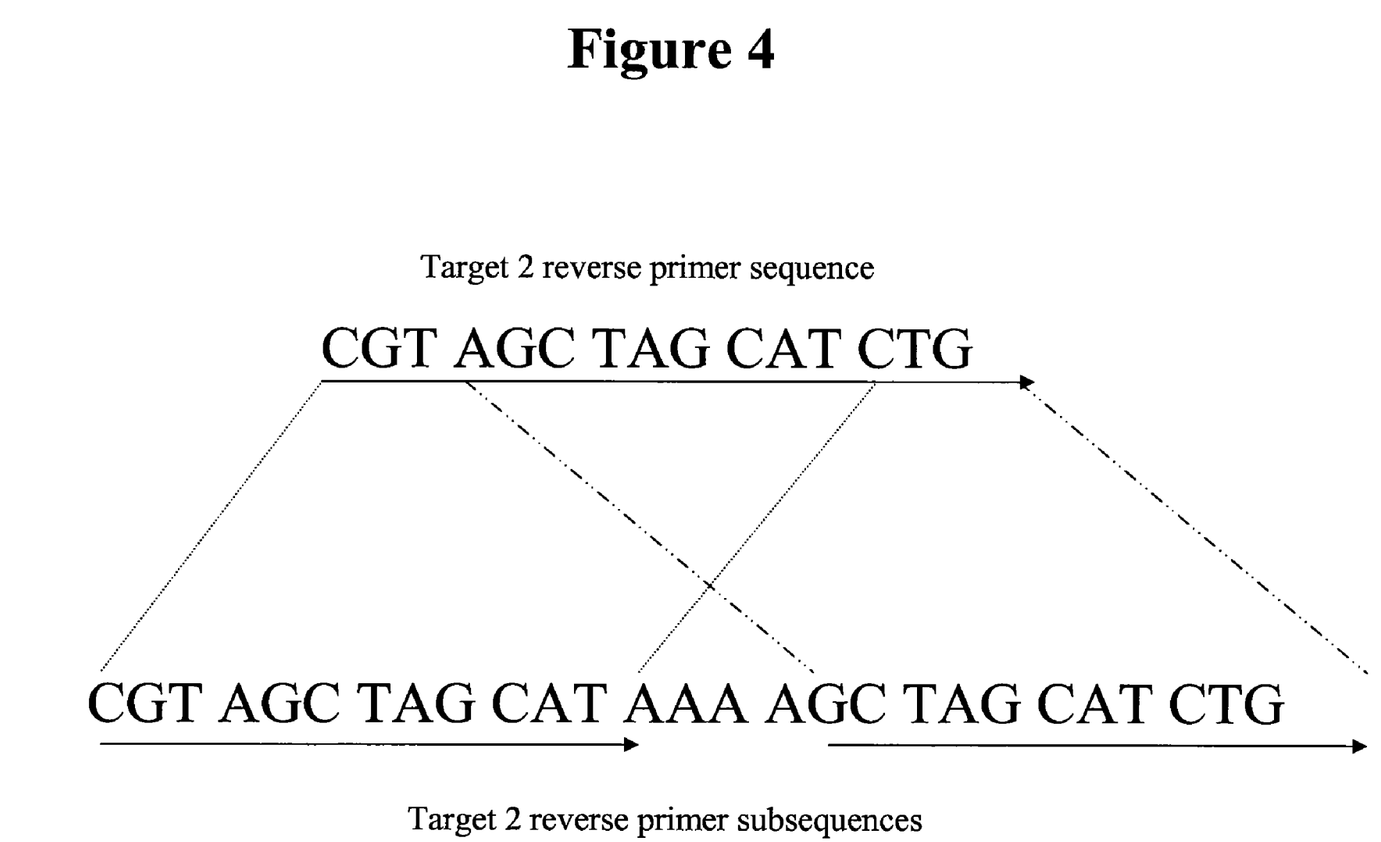
FIG. 4 illustrates one possible design for inserting primer subsequences into the single-stranded control polynucleotide. In the illustrated embodiment, the first 12 nucleotides and the last 12 nucleotides of a 15 mer primer sequence (SEQ ID NO:9) are each present in a single-stranded control polynucleotide. The two 12 mer sequences are separated by at least one unrelated nucleotide (N). In this embodiment, the two subsequences "overlap" in that the last nine nucleotides of the first subsequence are identical to the first nine nucleotides of the second subsequence. Target 2 reverse primer sequence=SEQ ID NO:9; Target 2 reverse primer subsequences=SEQ ID NO: 14.
Figure 5:
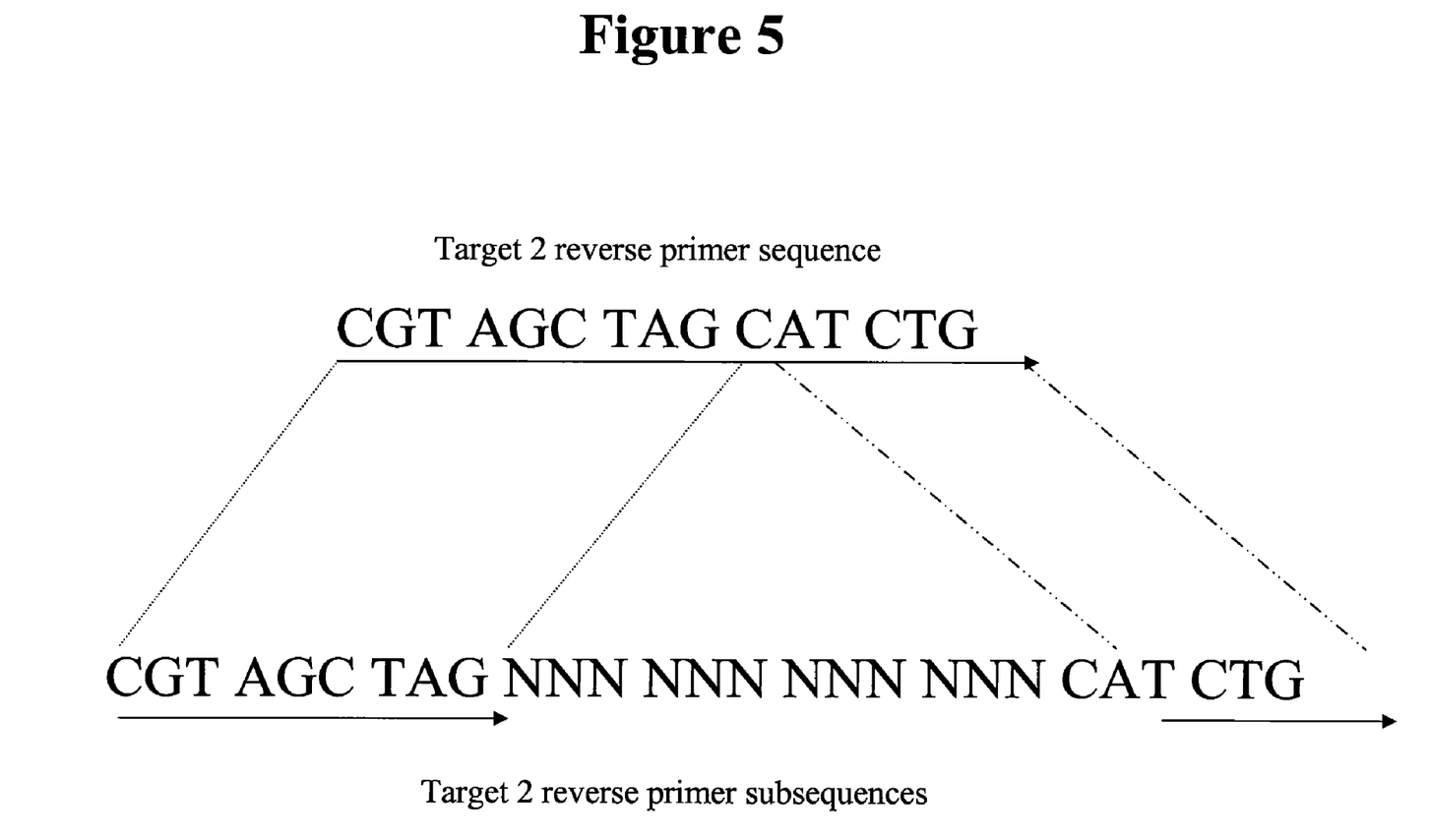
FIG. 5 illustrates another possible design for inserting primer subsequences into the single-stranded control polynucleotide. In the illustrated embodiment, a 15 mer primer sequence (SEQ ID NO:9) is divided into a 9 mer subsequence and a 6 mer subsequence, each of which are present in a single-stranded control polynucleotide. The subsequences are separated by at least one unrelated nucleotide (N). Target 2 reverse primer sequence=SEQ ID NO:9; Target 2 reverse primer subsequences=SEQ ID NO: 15.

FIGS. 4 and 5 represent two possible ways that primer subsequences can be designed. As illustrated in FIG. 4, subsequences of a primer sequence can be designed such that the 5' end of one subsequence comprises the same sequence as the 3' end of a second subsequence. In these embodiments, the subsequences are said to "overlap." Two or more overlapping sequences can be present in the control polynucleotide and can be present in any order. If desired, the subsequences can be separated by any number of other, unrelated base pairs.

FIG. 5 illustrates another option for creating multiple subsequences from a primer sequence. In this option, the subsequences do not overlap, but instead represent different fractions of the primer sequence. In the illustrated embodiment, every nucleotide of the primer sequence is represented in at least one subsequence. Of course, other embodiments are possible where the subsequences do not include every nucleotide of the primer sequence.

The multiplex amplification reaction can provide for as many amplification products as desired. The control polynucleotide, therefore, can have sequences or subsequences from as many different primers as are part of the multiplex reaction.

III. Amplification Reactions of the Invention

Amplification of an RNA or DNA template using reactions is well known (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal cycler to facilitate incubation times at desired temperatures. Degenerate oligonucleotides can be designed to amplify target DNA sequence homologs using the known sequences that encode the target DNA sequence.

Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

Isothermic amplification reactions are also known and can be used according to the methods of the invention. Examples of isothermic amplification reactions include strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J.*

Clin. Microbiol. 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)). Other amplification methods known to those of skill in the art include CPR (Cycling Probe Reaction), SSR (Self-Sustained Sequence Replication), SOA (Strand Displacement Amplification), QBR (Q-Beta Replicase), Re-AMP (formerly RAMP), RCR (Repair Chain Reaction), TAS (Transorbtion Based Amplification System), and HCS.

The methods of the invention can be used in multiplex reactions. Multiplex PCR results in the amplification of multiple polynucleotide fragments in the same reaction. See, e.g., PCR PRIMER, A LABORATORY MANUAL (Dieffenbach, ed. 1995) Cold Spring Harbor Press, pages 157-171. For instance, different target templates can be added and amplified in parallel in the same reaction vessel.

The concentration of the magnesium salt in the reaction mixture can be important when trying to copy different target DNA sequences. Thus, some variation of the concentration of the magnesium salt, e.g., magnesium chloride, may be required to optimize the reaction to amplify the target nucleic acid sequences of interest. One of skill can vary the concentration of magnesium salt or ion present in the reaction mixture to arrive at the proper conditions for amplification.

In some embodiments, the target polynucleotides in the multiplex amplification reaction are not products of nested primers. In these embodiments, the primers of the amplification reaction are sufficient to amplify target polynucleotides that are not subsequences of each other. In some embodiments, a first target sequence is less than about 95% identical, and preferably less than about 90%, 80%, 70%, 60% or 50% identical to any other target sequence in the amplification reaction.

IV. Detection of Amplified Polynucleotides

Numerous types of probes are capable of hybridizing to and detecting a particular polynucleotide sequences. In some cases, the probe also comprises a fluorophore or enzyme, as described below, which allows for the detection of the binding of the probe to its complement.

Probe concentration should be sufficient to bind to the amount of target or control sequences that are amplified so as to provide an accurate assessment of the quantity of amplified sequence. Those of skill in the art will recognize that the amount of concentration of probe will vary according to the binding affinity of the probe as well as the quantity of sequence to be bound. Typical probe concentrations will range from 0.01 µM to 0.5 µM.

The present invention can employ many different nucleic acid hybridization probes. Typically, for signal generation, the probes utilize a change in the fluorescence of a fluorophore due to a change in its interaction with another molecule or moiety brought about by changing the distance between the fluorophore and the interacting molecule or moiety. Alternatively, other methods of detecting a polynucleotide in a sample, including the use of radioactively-labeled probes, are provided.

Fluorescence-based assays typically rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L, *Ann. Rev. Biochem.* 47: 819-846 (1978); BIOPHYSICAL CHEMISTRY part II, Techniques for the Study of Biological Structure and Function, C. R. Cantor and P. R. Schimmel, pages 448-455 (W.H. Freeman and Co., San Francisco, U.S.A., 1980); and Selvin, P. R., *Methods in Enzymology* 246: 300-335 (1995). Efficient FRET interaction requires that the absorption and emission spectra of the pair have a large degree of overlap. The efficiency of FRET interaction is linearly proportional to that overlap. See Haugland, R. P. et al. *Proc. Natl. Acad. Sci. USA* 63: 24-30 (1969). Typically, a large magnitude of signal (i.e., a high degree of overlap) is required. FRET pairs, including fluorophore-quencher pairs, are therefore typically chosen on that basis.

A variety of labeled nucleic acid hybridization probes and detection assays that utilize FRET and FRET pairs are known. One such scheme is described by Cardullo et al. *Proc. Natl. Acad. Sci. USA* 85: 8790-8794 (1988) and in Heller et al. EP 0070685. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which in this application is meant an interactive moiety (or molecule) that releases the accepted energy as heat.

Another type of nucleic acid hybridization probe assay utilizing a FRET pair is the "TaqMan®" assay described in Gelfand et al. U.S. Pat. No. 5,210,015, and Livak et al. U.S. Pat. No. 5,538,848. The probe is a single-stranded oligonucleotide labeled with a FRET pair. In a TaqMan® assay, a DNA polymerase releases single or multiple nucleotides by cleavage of the oligonucleotide probe when it is hybridized to a target strand. That release provides a way to separate the quencher label and the fluorophore label of the FRET pair.

Yet another type of nucleic acid hybridization probe assay utilizing FRET pairs is described in Tyagi et al. U.S. Pat. No. 5,925,517, which utilizes labeled oligonucleotide probes, which are referred to as "Molecular Beacons." See Tyagi, S. and Kramer, F. R., *Nature Biotechnology* 14: 303-308 (1996). A Molecular beacon probe is an oligonucleotide whose end regions hybridize with one another in the absence of target but are separated if the central portion of the probe hybridizes to its target sequence. The rigidity of the probe-target hybrid precludes the simultaneous existence of both the probe-target hybrid and the intramolecular hybrid formed by the end regions. Consequently, the probe undergoes a conformational change in which the smaller hybrid formed by the end regions disassociates, and the end regions are separated from each other by the rigid probe-target hybrid. For molecular beacon probes, a central target-recognition sequence is flanked by arms that hybridize to one another when the probe is not hybridized to a target strand, forming a "hairpin" structure, in which the target-recognition sequence (which is commonly referred to as the "probe sequence") is in the single-stranded loop of the hairpin structure, and the arm sequences form a double-stranded stem hybrid. When the probe hybridizes to a target, that is, when the target-recognition sequence hybridizes to a complementary target sequence, a relatively rigid helix is formed, causing the stem hybrid to unwind and forcing the arms apart.

Non-FRET fluorescent probes, such as those described in, e.g., Tyagi et al., U.S. Pat. No. 6,150,097 ("the '097 patent"), can also be used. For example, the '097 patent describes how changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

V. Quantification of Probe Binding

Binding of a probe to its complementary hybridization sequence allows the user to quantify the accumulation of a particular sequence without necessarily removing the contents from the reaction vessel. In general, any type of label that allows for the detection and differentiation of different probes can be used according to the methods of the invention.

Accumulation of amplified product can be quantified by any method known to those in the art. For instance, fluorescence from a probe can be detected by measurement of light at a particular frequency. Similarly, the accumulation of various chemical products created via an enzymatic reaction linked to the probe can be measured, for instance, by measuring absorbance of light at a particular wavelength. In other embodiments, amplification reactions can be quantified directly by blotting them onto a solid support and hybridizing with a radioactive nucleic acid probe. Once unbound probe is washed away, the amount of probe can be quantified by measuring radioactivity as is known to those of skill in the art. Other variations of this technique employ the use of chemiluminescence to detect hybridization events.

Measurement of amplification products can be performed after the reaction has been completed or can be measured in "real time" (i.e., as the reaction occurs). If measurement of accumulated amplified product is performed after amplification is complete, then detection reagents (e.g. probes) can be added after the amplification reaction. Alternatively, probes can be added to the reaction prior or during the amplification reaction, thus allowing for measurement of the amplified products either after completion of amplification or in real time. Real time measurements are preferred because they allow for measurement at any given cycle of the reaction and thus provide more information about accumulation of products throughout the reaction. For measurement of amplification product in real time, the use of fluorescent probes is preferred.

VI. Kits and Solutions of the Invention

The invention also provides kits and solutions for carrying out the amplification methods of the invention. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a target sample.

Kits can include, for instance, amplification reagents comprising primers sufficient to amplify at least two different target sequences, a polynucleotide sequence comprising the sequences of the primers or subsequences of the primers s described herein; and at least one probe for amplifying and detecting the polynucleotide sequence. In addition, the kit can include nucleotides (e.g., A, C, G and T), a DNA polymerase and appropriate buffers, salts and other reagents to facilitate amplification reactions.

In some embodiments, the kits comprise vessels such as sample processing cartridges useful for rapid amplification of a sample as described in Belgrader, P., et al., *Biosensors and Bioelectronics* 14:849-852 (2000); Belgrader, P., et al., *Science,* 284:449-450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

EXAMPLES

The following example is offered to illustrate, but not to limit the claimed invention.

Example 1

This example shows a multiplex PCR reaction to test for the presence of Bacteria A and Bacteria B in a sample.

In this example, primer sequences are highlighted for the convenience of the reader. Bacteria A has the following specific PCR target sequence:

(SEQ ID NO: 1)
5' GGT GCG AAA GTG TAA CGA GGT GGA AAG CGC ACC ATC GTT TCT ATT ACA AGT CCC TTG ATG GAA GAT TAT GTC GAC CAC TTT 3'

The complimentary sequence to the target sequence for Bacteria A is shown below:

(SEQ ID NO: 2)
3' CCA CGC TTT CAC ATT GCT CCA CCT TTC GCG TGG TAG CAA AGA TAA TGA TCA GGG AAC TAC CTT CTA ATA CAG CTG GTG AAA 5'

The primer set of Bacteria A is:

Forward = 5' TTA CAC TTC CGC ACC 3' (SEQ ID NO: 3)

Reverse = 5' TAT GTC GAC CAC TTT 3' (SEQ ID NO: 4)

The probe for Bacteria A is a Beacons probe with the following sequence:

(SEQ ID NO: 5)
FAM-5' CCA CGC ACT AGT AAT AGA AAC GCG TGG 3' - DABCYL

Bacteria B has this specific PCR target sequence:

(SEQ ID NO: 6)
5' GCA CGC GTA TGC AGC GAC GAT GCA GCG ACG AGT CGA GGC TAG GCG AGC AGC TTT ATC TAT CAT CGT GAT CGT GTA CGT AGC TAG CAT CTG 3'

The complimentary sequence to the target sequence for Bacteria B is shown below:

(SEQ ID NO: 7)
3' CGT GCG CAT ACG TCG CTG CTA CGT CGC TGC TCA GCT CCG ATC CGC TCG TCG AAA TAG ATA GTA GCA CTA GCA CAT GCA TCG ATC GTA GAC 5'

The primer set of Bacteria B is:

Forward = 5' GCT GCA TAC GCG TGC 3' (SEQ ID NO: 8)

Reverse = 5' CGT AGC TAG CAT CTG 3' (SEQ ID NO: 9)

The probe for Bacteria B is a Beacons probe with the following sequence:

(SEQ ID NO: 10)
Texas Red - 5' CCA CGC GCT GCT CGC CTA GCC TCG GCG TGG 3' - DABCYL An Internal Control Oligo is produced with the following sequence:

(SEQ ID NO: 11)
5' GGT GCG GAA GTG TAA AAA CGT AGC TAG CAT AAA AGC TAG CAT CTG AAA TCG AGC TGA TGC TGC AAA GCT GCA TAC GCG AAA GCA TAC GCG TGC AAA TAT GTC GAC CAC TTT 3'

The complimentary sequence to the target sequence for the Internal Control Oligo is shown below:

(SEQ ID NO: 12)
3' CCA CGC CTT CAC ATT TTT GCA TCG ATC GTA TTT TCG ATC GTA GAC TTT AGC TCG ACT ACG ACG TTT CGA CGA ATG CGC TTT CGT ATG CGC ACG TTT ATA CAG CTG GTG AAA 5'

The Internal Control utilizes the same primers as Bacteria A.

Forward = 5' TTA CAC TTC CGC ACC 3' (SEQ ID NO: 3)

Reverse = 5' TAT GTC GAC CAC TTT 3' (SEQ ID NO: 4)

The probe for the Internal Control is a Beacons probe with the following sequence:

(SEQ ID NO: 13)
TET - 5' CCA CGC GCA GCA TCA GCT CGA GCG TGG 3' - DABCYL

Note, in this example, only the forward strand of the Internal Control Oligo is added to the PCR reaction. As a control for the integrity of the primers in the reaction, the Internal Control Oligo, like the primers, is single-stranded. The compliment of the Internal Control Oligo is produced by the PCR reaction.

Since the Internal Control Oligo contains the primer sequences for Bacteria B and is amplified by primers for Bacteria A, any sequence specific degradation of the Bacteria A or B primer sequences will also prevent amplification of the Internal Control Oligo. The sequence for the primers of Bacteria B also have been divided into subsequences to prevent Bacteria B primers from hybridizing to the Bacteria B primer sequences in the Internal Control Oligo during PCR. However, the Bacteria B primer subsequences contain enough of the Bacteria B primer sequence to allow for recognition by sequence specific endonuclease activity of the Bacteria B primers if that activity exists in the sample.

If there is general primer degradation (affecting both Bacteria A and Bacteria B primer sets) then the internal control will not amplify because the Internal Control Oligo uses the primers from the Bacteria A test.

If one of the primers from the Bacteria A test is specifically destroyed by nuclease activity then the Internal Control Oligo will not be amplified because it utilizes the primers of the Bacteria A test. If one of the primers from the Bacteria B test is specifically destroyed by nuclease activity, then the Internal Control target sequence will also be destroyed because the Internal Control Oligo contains the same sequence as the Bacteria B primers. Thus, amplification of the Internal Control Probe, and thus binding of the Internal Control Oligo-specific Beacon, only occurs if neither Bacteria A or B primer sequences are degraded.

The primers, probes, and Internal Control are mixed with other PCR components as follows:

| Component | Vol/25 ul reaction | Final Conc |
|---|---|---|
| Water | 1.725 | |
| Bacteria A Forward Primer (10 μM) | 0.5 | 400 nM |
| Bacteria A Reverse Primer (10 μM) | 0.5 | 400 nM |
| Bacteria B Forward Primer (10 μM) | 0.5 | 400 nM |
| Bacteria B Reverse Primer (10 μM) | 0.5 | 400 nM |
| Bacteria A Probe (10 μM)-FAM | 0.5 | 400 nM |
| Bacteria B Probe (10 pM)-Texas Red | 0.5 | 400 nM |
| Internal Control Probe (10 μM) - TET | 0.5 | 400 nM |
| Internal Control Target Oligo* | 0.5 | 10 nM |
| MgCl2 (50 mM) | 3 | 6 mM |
| dNTPs (10 mM) | 0.4 | 160 μM |
| 10x PCR buffer | 2.5 | 1x |
| Taq Polymerase (5 U/μl) | 0.25 | 1.25 U |

-continued

| Component | Vol/25 ul reaction | Final Conc |
|---|---|---|
| DNA Sample | 12.5 | 12.5 μl |
| Total vol | 25 | |

The PCR mix is then cycled in a thermocycler with real-time optics capabilities such as the Smart Cycler® with the following PCR conditions:

| Stage 1 | Stage 2 |
|---|---|
| Repeat 1 time | Repeat 45 times |
| 95° 180 sec | 95° 5 sec |
| | 56° 14 sec - optics on |
| | 72° 5 sec |

Note:
PCR conditions may vary.

At the end of the PCR reaction, the signal for Bacteria A and Bacteria B may or may not be positive based on the DNA sample. However, the signal for the internal control sequence should be positive. If it is not, then the PCR test is flagged as invalid (unless both Bacteria A and Bacteria B are positive, indicating that the primer integrity remained intact and the Internal Control is not needed).

If the internal control is negative, it could indicate a problem with the primers. There could be either general degradation of all primers, or of a specific endonuclease that affects only one primer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reagent kit, comprising,
   i. at least one fluorescently-labeled nucleic acid probe;
   ii. a first primer pair comprising a first and second primer, wherein the first primer pair is sufficient to amplify a first target sequence by polymerase chain reaction;
   iii. a second primer pair and a third primer pair sufficient to amplify a second and third target sequence, respectively, by polymerase chain reaction;
   iv. a single-stranded control polynucleotide comprising:
      (a) a nucleotide sequence of the first primer and a nucleotide sequence (designated a "second primer binding sequence") that is complementary to the second primer; and
      (b) located between said nucleotide sequence of the first primer and said second primer binding sequence:
         (1) the sequences of the primers of the second and third primer pairs or subsequences thereof that are at least 5 nucleotides long, and
         (2) a probe binding sequence that is complementary to said fluorescently-labeled nucleic acid probe;
      wherein said nucleic acid probe is sufficiently complementary to said probe binding site to allow for detection of said single-stranded control polynucleotide sequence.

2. The reagent kit of claim 1, wherein the single-stranded control polynucleotide sequence is a synthetic single-stranded polynucleotide.

3. The reagent kit of claim 1, where the single-stranded control polynucleotide sequence comprises each of the primer sequences.

4. The reagent kit of claim 1, wherein the single-stranded control polynucleotide sequence comprises two or more subsequences of the primers at least five nucleotides long, wherein the two or more subsequences are not contiguous in the single-stranded polynucleotide sequence.

5. The reagent kit of claim 1, wherein the single-stranded control polynucleotide sequence comprises at least two subsequences of each primer, wherein the combination of the at least two subsequences contain every nucleotide of the primer sequence, wherein the two or more subsequences are not contiguous in the single-stranded polynucleotide sequence.

6. The reagent kit of claim 1, wherein the single-stranded control polynucleotide sequence comprises two subsequences of a primer sequence, wherein the two or more subsequences are not contiguous in the single-stranded polynucleotide sequence, and at least the last two nucleotides of a first subsequence are identical to the first at least two nucleotides of a second sequence.

7. The reagent kit of claim 6, wherein at least the last five nucleotides of the first subsequence are identical to at least the first five nucleotides of the second subsequence.

8. The reagent kit of claim 1, further comprising at least one reaction vessel.

9. The reagent kit of claim 1, further comprising nucleotides.

10. The reagent kit of claim 1, further comprising a DNA polymerase.

11. The reagent kit of claim 1, wherein the single-stranded polynucleotide sequence comprises sequences, or a complement thereof, of primers of the first primer pair oriented such that the first primer pair is capable of amplifying the remaining primer sequences, or subsequences thereof, in the single-stranded polynucleotide.

12. The reagent kit of claim 1, wherein the single-stranded polynucleotide sequence comprises all subsequences of the primers that are nine nucleotides long, wherein the subsequences are not contiguous in the single-stranded polynucleotide sequence.

13. The reagent kit of claim 1, the single-stranded polynucleotide sequence comprises sequences or subsequences of the second primer pair oriented such that the reverse primer sequence of the second primer pair or subsequence thereof is closer to the 5' end of the polynucleotide sequence than the forward primer sequence of the second primer pair, or subsequence thereof.

14. The reagent kit of claim 1, wherein the single-stranded polynucleotide comprises the sequences of each primer of the first primer pair and the second primer pair.

* * * * *